United States Patent
Nelson et al.

(10) Patent No.: US 8,172,763 B2
(45) Date of Patent: May 8, 2012

(54) IMAGING AND ANALYSIS OF MOVEMENT OF ERYTHROCYTES IN BLOOD VESSELS IN RELATION TO THE CARDIAC CYCLE

(75) Inventors: Darin Nelson, Misgav Dov (IL); Arik Drori, Tel Aviv (IL); Amiram Grinvald, Rehovot (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 685 days.

(21) Appl. No.: 11/919,815

(22) PCT Filed: May 8, 2006

(86) PCT No.: PCT/US2006/017645
§ 371 (c)(1),
(2), (4) Date: Feb. 25, 2009

(87) PCT Pub. No.: WO2006/121984
PCT Pub. Date: Nov. 16, 2006

(65) Prior Publication Data
US 2009/0221912 A1    Sep. 3, 2009

Related U.S. Application Data

(60) Provisional application No. 60/678,238, filed on May 6, 2005.

(51) Int. Cl.
*A61B 5/02* (2006.01)
(52) U.S. Cl. .................................................. 600/508
(58) Field of Classification Search .................. 361/695; 416/179; 415/211.2, 191, 116, 201; 15/104.068, 15/1.7, 387, 344, 256.52, 385; 417/423.2; 600/508
See application file for complete search history.

(56) References Cited

U.S. PATENT DOCUMENTS

| | | | |
|---|---|---|---|
| 4,621,643 A | 11/1986 | New, Jr. et al. |
| 4,718,417 A | 1/1988 | Kittrell et al. |
| 4,998,533 A | 3/1991 | Winkelman |
| 5,217,456 A | 6/1993 | Narciso, Jr. |
| 5,240,006 A | 8/1993 | Fujii et al. |
| 5,279,298 A | 1/1994 | Flower |
| 5,348,003 A | 9/1994 | Caro |
| 5,400,091 A | 3/1995 | Okazaki |
| 5,463,426 A | 10/1995 | Grinvald |

(Continued)

FOREIGN PATENT DOCUMENTS

| CN | 2151483 | 10/1993 |
|---|---|---|
| EP | 1 302 158 | 4/2003 |
| WO | WO 99/63882 | 12/1999 |
| WO | WO 00/06015 | 2/2000 |
| WO | WO 01/22741 | 3/2001 |
| WO | WO 2004/004556 | 1/2004 |

OTHER PUBLICATIONS

A Supplementary European Search Report dated Sep. 25, 2009, which issued during the prosecution of Applicant's European Patent Application No. EP 06 75 9270.

(Continued)

*Primary Examiner* — George Manuel
(74) *Attorney, Agent, or Firm* — Abelman, Frayne & Schwab

(57) ABSTRACT

Apparatus (2) is provided, including a heartbeat measurement device (3), which senses a cardiac parameter of a patient and generates a cardiac parameter signal responsively thereto. An optical measurement device acquires data by emitting towards tissue of the patient 400-1000 nm light, and receiving light reflected from the tissue. An integrator unit (10) receives the cardiac parameter signal and, in response thereto, actuates the optical measurement device to acquire the data.

29 Claims, 4 Drawing Sheets

U.S. PATENT DOCUMENTS

| | | | |
|---|---|---|---|
| 5,515,847 A | 5/1996 | Braig et al. | |
| 5,572,996 A | 11/1996 | Doiron et al. | |
| 5,598,842 A | 2/1997 | Ishihara et al. | |
| 5,666,956 A | 9/1997 | Buchert | |
| 5,706,821 A | 1/1998 | Matcher et al. | |
| 5,720,291 A | 2/1998 | Schwartz | |
| 5,722,398 A | 3/1998 | Ishihara et al. | |
| 5,741,213 A | 4/1998 | Kouchi et al. | |
| 5,769,076 A | 6/1998 | Maekawa et al. | |
| 5,784,162 A | 7/1998 | Cabib | |
| 5,787,185 A | 7/1998 | Clayden | |
| 5,791,345 A | 8/1998 | Ishihara et al. | |
| 5,811,814 A | 9/1998 | Leone et al. | |
| 5,931,779 A | 8/1999 | Arakaki et al. | |
| 5,934,278 A | 8/1999 | Ishihara et al. | |
| 5,974,338 A | 10/1999 | Asano et al. | |
| 5,983,120 A | 11/1999 | Groner | |
| 6,061,583 A | 5/2000 | Ishihara et al. | |
| 6,081,612 A | 6/2000 | Krusin et al. | |
| 6,088,087 A | 7/2000 | Graves et al. | |
| 6,104,939 A | 8/2000 | Groner et al. | |
| 6,208,749 B1 | 3/2001 | Krusin et al. | |
| 6,244,712 B1 | 6/2001 | Smith et al. | |
| 6,350,431 B1 | 2/2002 | Snow et al. | |
| 6,351,663 B1 | 2/2002 | Flower | |
| 6,362,175 B1 | 3/2002 | Vinogradov et al. | |
| 6,512,936 B1 | 1/2003 | Monfre et al. | |
| 6,512,937 B2 | 1/2003 | Blank et al. | |
| 6,567,678 B1 | 5/2003 | Oosta et al. | |
| 6,571,118 B1 | 5/2003 | Utzinger et al. | |
| 6,587,701 B1 | 7/2003 | Stranc et al. | |
| 6,588,901 B1 | 7/2003 | Grinvald et al. | |
| 6,721,582 B2 | 4/2004 | Trepagnier et al. | |
| 6,782,289 B1 | 8/2004 | Strauss | |
| 6,826,424 B1 | 11/2004 | Zeng et al. | |
| 6,844,195 B2 | 1/2005 | Craine | |
| 6,859,658 B1 | 2/2005 | Krug | |
| 6,869,430 B2 | 3/2005 | Balbierz et al. | |
| 6,889,075 B2 | 5/2005 | Marchitto et al. | |
| 6,898,451 B2 | 5/2005 | Wuori | |
| 6,898,458 B2 | 5/2005 | Zeng et al. | |
| 6,902,935 B2 | 6/2005 | Kaufman | |
| 6,917,038 B2 | 7/2005 | Zheng et al. | |
| 7,025,765 B2 | 4/2006 | Balbierz et al. | |
| 7,054,674 B2 | 5/2006 | Cane et al. | |
| 7,115,841 B2 | 10/2006 | Zeng et al. | |
| 7,190,452 B2 | 3/2007 | Zeng et al. | |
| 7,217,266 B2 | 5/2007 | Anderson et al. | |
| 7,225,005 B2 | 5/2007 | Kaufman et al. | |
| 7,253,894 B2 | 8/2007 | Zeng et al. | |
| 2001/0031920 A1 | 10/2001 | Kaufman et al. | |
| 2001/0056237 A1 | 12/2001 | Cane et al. | |
| 2002/0007122 A1 | 1/2002 | Kaufman et al. | |
| 2002/0007123 A1 | 1/2002 | Balas | |
| 2002/0016533 A1* | 2/2002 | Marchitto et al. | 600/310 |
| 2002/0016534 A1 | 2/2002 | Trepagnier et al. | |
| 2002/0026127 A1 | 2/2002 | Balbierz et al. | |
| 2002/0026188 A1 | 2/2002 | Balbierz et al. | |
| 2002/0076820 A1 | 6/2002 | Craine | |
| 2002/0103439 A1 | 8/2002 | Zeng et al. | |
| 2002/0111545 A1 | 8/2002 | Lindberg | |
| 2002/0127735 A1 | 9/2002 | Kaufman et al. | |
| 2002/0197728 A1 | 12/2002 | Kaufman et al. | |
| 2003/0032064 A1 | 2/2003 | Soller et al. | |
| 2003/0036693 A1 | 2/2003 | Avinash et al. | |
| 2003/0036751 A1 | 2/2003 | Anderson et al. | |
| 2003/0050541 A1 | 3/2003 | Wuori | |
| 2003/0114762 A1 | 6/2003 | Balas et al. | |
| 2003/0146385 A1 | 8/2003 | Zheng et al. | |
| 2003/0163049 A1 | 8/2003 | Balas | |
| 2003/0207250 A1 | 11/2003 | Kaufman et al. | |
| 2004/0015211 A1 | 1/2004 | Nurmikko et al. | |
| 2004/0044287 A1 | 3/2004 | Lin et al. | |
| 2004/0116814 A1 | 6/2004 | Stranc et al. | |
| 2005/0054936 A1 | 3/2005 | Balas | |
| 2005/0064602 A1 | 3/2005 | Kaufman et al. | |
| 2005/0090751 A1 | 4/2005 | Balas | |
| 2005/0131284 A1 | 6/2005 | Grinvald et al. | |
| 2005/0143662 A1 | 6/2005 | Marchitto et al. | |
| 2005/0167621 A1 | 8/2005 | Zeng et al. | |
| 2005/0192493 A1 | 9/2005 | Wuori | |
| 2005/0203421 A1 | 9/2005 | Zeng et al. | |
| 2005/0203423 A1 | 9/2005 | Zeng et al. | |
| 2005/0251049 A1 | 11/2005 | Cane et al. | |
| 2006/0122524 A1 | 6/2006 | Kawada et al. | |
| 2006/0141633 A1 | 6/2006 | Balas | |
| 2006/0195022 A1 | 8/2006 | Trepagnier et al. | |
| 2006/0241577 A1 | 10/2006 | Balbierz et al. | |
| 2007/0043341 A1 | 2/2007 | Anderson et al. | |

OTHER PUBLICATIONS

U. Seifert, W. Visler, "Retinal Vessel Analyzer (RVA)—Design and Function", Biomed Tech vol. 47, Suppl. 1, 2002.

Sato Y et al., "Automatic extraction and measurement of leukocyte motion in microvessels using spatiotemporal image analysis", IEEE Trans. on Biomedical Engineering, IEEE Inc. New York, US, vol. 44, No. 4, Apr. 1, 1997.

Holeman B et al., "Dynamic scene analysis for vessel structure determination", Southeastcon '89 proceedings, Energy and information technologies in the southeast, Columbia, SC, USA, Apr. 9, 1989, pp. 1072-1073.

Domingo J et al., "Irregular motion recovery in flourescein angiograms", Pattern Recognition Letters, North-Holland Publ. Amsterdam, vol. 18, No. 8, Aug. 1, 1997, pp. 805-821.

Sklenar J et al., "Parametric imaging for myocardial contrast echocardiography: pixel-by-pixel incorporation of information from both spatial and temporal domains", Computer in Cardiology 1998 Cleveland, OH, USA, Sep. 13-16, 1998, pp. 461-464.

R.A. Linsenmeier, et al., "Metabolic dependence of photoreceptors on the choroids in the normal and detached retina", Published in Investigative Ophthalmology and Visual Science, vol. 41(10), pp. 3117-3123, Sep. 2000.

R.A. Linsenmeier, et al., "Retinal hypoxia in long-term diabetic cats", Published in Investigative Ophthalmology and Visual Science, vol. 39(9), pp. 1647-1657, Aug. 1998.

Kurt R. Denninghoff, et al., "Retinal imaging techniques in diabetes", Published in Diabetes Technology & Therapeutics, vol. 2, No. 1, 2000, pp. 111-113.

M. Bruce Shields, "Textbook of Glaucoma", Published by Lippincott Williams and Wilkins (Philadelphia), 1997.

Wong T.Y. et al., "White matter lesions, retinopathy, and incident clinical stroke", JAMA 288(1), pp. 67-74, 2002.

Wong T.Y. et al., "Retinal arteriolar narrowing and risk coronary heart disease in men and women. The atherosclerosis risk in communities study", JAMA; 287(9), pp. 1153-1159, 2002.

H.H. Quick, et al., "MR Imaging of the Vessel wall", Published in Eur. Radiol, vol. 12(4), pp. 889-900, Apr. 2002.

Dormandy, et al., "Lower-extremity arteiosclerosis as a reflection of a systemic process: implications for concomitant coronary and carotid disease", Published in Semin. Vasc. Surg. pp. 118-122, vol. 12(2), Jun. 1999.

Kutzner, et al., "Fatal lipid embolism following intra-arterial angiography at an early stage of anteriosclerosis", Published in British Journal of Radiology, vol. 73 (874), pp. 1108-1111, Oct. 2000.

Wong T.Y. et al., "Retinal microvascular abnormalities and incident stroke: the atherosclerosis risk in communities study", Lancet, 358 (9288), pp. 1134-1140, 2001.

"Finite element modeling of three-dimensional pulsatile flow in the abdominal aorta: Relevance to atherosclerosis," Taylor et al., Annals of Biomedical Engineering, vol. 26, pp. 975-987, 1998.

"In vivo quantification of blood flow and wall shear stress in the human abdominal aorta during lower limb exercise," Taylor et al., Annals of Biomedical Engineering, vol. 30, pp. 402-408, 2002.

Michelson G. et al., "Flickering light increases retinal blood flow", Retina, 22(3): 336-343, Jun. 2002.

Grinvald A. et al., "In-vivo optical imaging of cortical architecture and dynamics", Published in Modern Techniques in Neuroscience Research, U. Windhorst and H. Johansson (eds.), Springer Verlag.

An Office Action dated Mar. 20, 2009 which issued during the prosecution of Applicant's Chinese Patent Application No. 2006800243350.

An Office Action dated Dec. 21, 2010, which issued during the prosecution of Applicant's European Patent Application No. EP 06 759 270.

* cited by examiner

DURATION OF $B_2 = \frac{T_2}{T_1} \cdot$ DURATION OF $B_1$

IMAGING AND ANALYSIS OF MOVEMENT OF ERYTHROCYTES IN BLOOD VESSELS IN RELATION TO THE CARDIAC CYCLE

CROSS-REFERENCES TO RELATED APPLICATIONS

The present patent application claims the priority of U.S. Provisional Patent Application 60/678,238 to Nelson et al., filed May 6, 2005, which is incorporated herein by reference.

FIELD OF THE INVENTION

The present invention relates generally to analyzing sampled biological data, and specifically to reducing error in sampled data.

BACKGROUND OF THE INVENTION

Diseases involving the retinal vasculature are one of the leading causes of blindness worldwide. Many of these diseases are both progressive and treatable. Thus, their early detection is highly desirable. Diagnoses are often made on the basis of the many obvious structural changes which may occur in the retina as a consequence of problems with retinal blood flow. These include neovascularization (the growth of new blood vessels in an attempt to compensate for a reduction in flow through pre-existing vessels), cotton-wool patches (regions in which nerve fiber axoplasmic transport has failed), and eventually the degeneration of retinal nerve fibers. Once observed, these and other phenomena may be used to diagnose retinal vascular disease, and treatment may begin to inhibit further degeneration. However, it is desirable to detect such problems early, if possible, before irreversible damage has occurred. Thus, attention has focused on developing methods of diagnosing retinal vasculature problems by measuring the rate of retinal blood flow, a reduction of which occurs prior to later, more serious, problems.

U.S. Pat. No. 6,588,901 to Grinvald et al., which is incorporated herein by reference, describes a system for directly imaging and analyzing the movement of individual erythrocytes in blood vessels. The system includes imaging means for acquiring, within a predetermined time interval from each other, at least one pair of images of at least one same erythrocyte for producing at least two frames, each image representing an analog or digital image of the location of the erythrocyte in each of the frames at a predetermined time. The system also includes image acquisition means for collecting and storing analog or digital images in machine-readable form, and a computer for controlling the operation of the imaging means and the image acquisition means, for processing the at least two frames, and for analyzing the movement of the erythrocyte in the blood vessels. A method for directly imaging and analyzing the movement of individual erythrocytes in blood vessels is also described.

An article by Michelson G et al., entitled, "Flickering light increases retinal blood flow," Retina, 22(3):336-343, June 2002, which is incorporated herein by reference, describes the examination of retinal blood flow in normal eyes before and during retinal stimulation by flickering light. Laser Doppler flowmetry measurements are described as having been synchronized with the electrocardiogram, in order to decrease the influence of the heartbeat on pulsation of retinal blood flow. As described, only phases similar in terms of the systolic or diastolic phase within the heart cycle were compared.

An article by Grinvald A. et al., entitled, "In-vivo optical imaging of cortical architecture and dynamics," published in Modern Techniques in Neuroscience Research, U. Windhorst and H. Johansson (eds.), Springer Verlag, which is incorporated herein by reference, describes imaging the brain, and various techniques for reducing the effect of heartbeat-induced and respiration-induced motion of the brain.

SUMMARY OF THE INVENTION

In some embodiments of the present invention, measurement apparatus comprises (a) an optical measurement device, which generates a burst of light and assesses a physiological parameter of a patient such as erythrocyte movement in the patient's blood vessels in response to reflected light, (b) a heartbeat measurement device, which senses a cardiac parameter of a patient, and (c) an integrator unit, which receives input from the heartbeat measurement device and triggers operation of the optical measurement device. Typically, but not necessarily, the optical measurement device comprises a non-invasive retinal scanner.

The light emitted by the optical measurement device typically comprises visible or near infrared light and/or has a wavelength in the range of 400-1000 nm.

There is therefore provided, in accordance with an embodiment of the invention, apparatus, including:

a heartbeat measurement device, which is operative to sense a cardiac parameter of a patient and to generate a cardiac parameter signal responsively thereto;

an optical measurement device, which is operative to acquire data by emitting towards tissue of the patient 400-100 nm light, and receiving light reflected from the tissue; and an integrator unit, which is operative to receive the cardiac parameter signal and, in response thereto, to actuate the optical measurement device to acquire the data.

In an embodiment, the optical measurement device includes a fundus camera.

In an embodiment, the optical measurement device includes an opthalmoscope.

In an embodiment, the heartbeat measurement device includes an electrocardiograph.

In an embodiment, the heartbeat measurement device includes a pulse oximeter.

In an embodiment, the heartbeat measurement device includes an optical densitometer.

In an embodiment, the cardiac parameter signal includes a digital pulse indicative of a heartbeat, and wherein the heartbeat measurement device is operative to generate the digital pulse and not to generate, every heartbeat, additional information indicative of a measured parameter of the heartbeat.

In an embodiment, the tissue includes a retina of the patient, and the optical measurement device is operative to receive light reflected from the retina.

In an embodiment, the tissue includes a tissue selected from the group consisting of: conjunctiva, episclera, tongue, a surface-accessible vascular bed, esophagus, stomach, small intestine, colon, an internal surface of a gastrointestinal tract, a vascularized passageway, heart, brain, liver, a surface of a surgically-accessible organ, and a vascular bed to which access is obtained by catheter, endoscopy, microendoscopy, or laparoscopy, and wherein the optical measurement device is operative to receive light reflected from the selected tissue.

In an embodiment, the cardiac parameter signal includes a varying trace indicative of a plurality of parameters of a single heartbeat, and wherein the heartbeat measurement device is operative to generate the varying trace.

In an embodiment, the integrator unit is operative to estimate a duration of a current, not yet completed, heartbeat responsively to (a) a portion of the varying trace indicative of parameters of a completed previous heartbeat, and (b) a portion of the varying trace indicative of parameters of the current heartbeat.

In an embodiment, the integrator unit is operative to designate a time for actuating the optical measurement device responsively to timing data from the heartbeat measurement device indicative of a duration of a prior heartbeat.

In an embodiment, the integrator unit is operative to receive during a current heartbeat an operator command from a human operator, indicating a readiness to acquire data, and to actuate the optical measurement device to acquire the data during the current heartbeat, responsively to the timing data indicative of the duration of the prior heartbeat.

In an embodiment, the integrator unit is operative to receive during a current heartbeat an operator command from a human operator, indicating a readiness to acquire data, and to actuate the optical measurement device to acquire the data during a heartbeat immediately following the current heartbeat, responsively to the timing data indicative of the duration of the prior heartbeat.

In an embodiment:

the designated time includes a plurality of designated times, the integrator unit is operative to designate the plurality of times as suitable for actuating the optical measurement device responsively to the timing data, and the integrator unit is operative to receive an operator command from a human operator, indicating a readiness to acquire data, and to actuate the optical measurement device to acquire the data at one of the designated times, responsively to the operator command.

In an embodiment, the integrator unit is operative to designate the time responsively to timing data indicative of a trend relating durations of a plurality of previous heartbeats.

In an embodiment, the integrator unit is operative to designate the time for actuating the optical measurement device responsively to timing data from the heartbeat measurement device indicative of a duration of an immediately previous heartbeat.

In an embodiment, the integrator unit is operative to:

(a) actuate the optical measurement device at the designated time during a current heartbeat, (b) subsequently determine the duration of the current heartbeat, (c) process data acquired by the optical measurement device according to a first protocol if the duration of the previous heartbeat differs from the duration of the current heartbeat by less than a threshold value, and (d) process data acquired by the optical measurement device according to a second protocol if the duration of the previous heartbeat differs from the duration of the current heartbeat by more than the threshold value.

In an embodiment, to carry out the first protocol the integrator unit is operative to designate the acquired data as good data.

In an embodiment, to carry out the first protocol the integrator unit is operative to process and output the acquired data for display to a human operator.

In an embodiment, the integrator-unit is operative to determine that the duration of the previous heartbeat (Dp) and the duration of the current heartbeat (Dc) differ by less than the threshold value if $1-\text{MIN}(Dp,Dc)/\text{MAX}(Dp,Dc)$ is less than 0.20.

In an embodiment, the integrator unit is operative to determine that the duration of the previous heartbeat (Dp) and the duration of the current heartbeat (Dc) differ by less than the threshold value if $\text{ABS}(Dp-Dc)$ is less than 50 ms.

In an embodiment, to carry out the second protocol the integrator unit is operative to discard the acquired data.

In an embodiment, to carry out the second protocol the integrator unit is operative to correct the acquired data, and output the corrected data for display to a human operator.

In an embodiment, the integrator unit is operative to analyze the acquired data to generate an indicator of blood flow velocity, and to correct the indicator of blood flow velocity by a factor that is based on a known relationship between typical blood flow velocities at a plurality of phases of a cardiac cycle.

There is also provided, in accordance with an embodiment of the invention, apparatus, including:

a cyclic-physiological-parameter measurement device, which is operative to sense a cyclically-varying parameter of a patient and to generate a cyclically-varying-parameter signal responsively thereto;

an optical measurement device, which is operative to acquire data by emitting light towards tissue of the patient and receiving light reflected from the tissue; and an integrator unit, which is operative to receive the cyclically-varying-parameter signal and, in response thereto, to actuate the optical measurement device to acquire the data.

The present invention will be more fully understood from the following detailed description of embodiments thereof, taken together with the drawings, in which:

DETAILED DESCRIPTION OF EMBODIMENTS OF THE INVENTION

Figure 1:
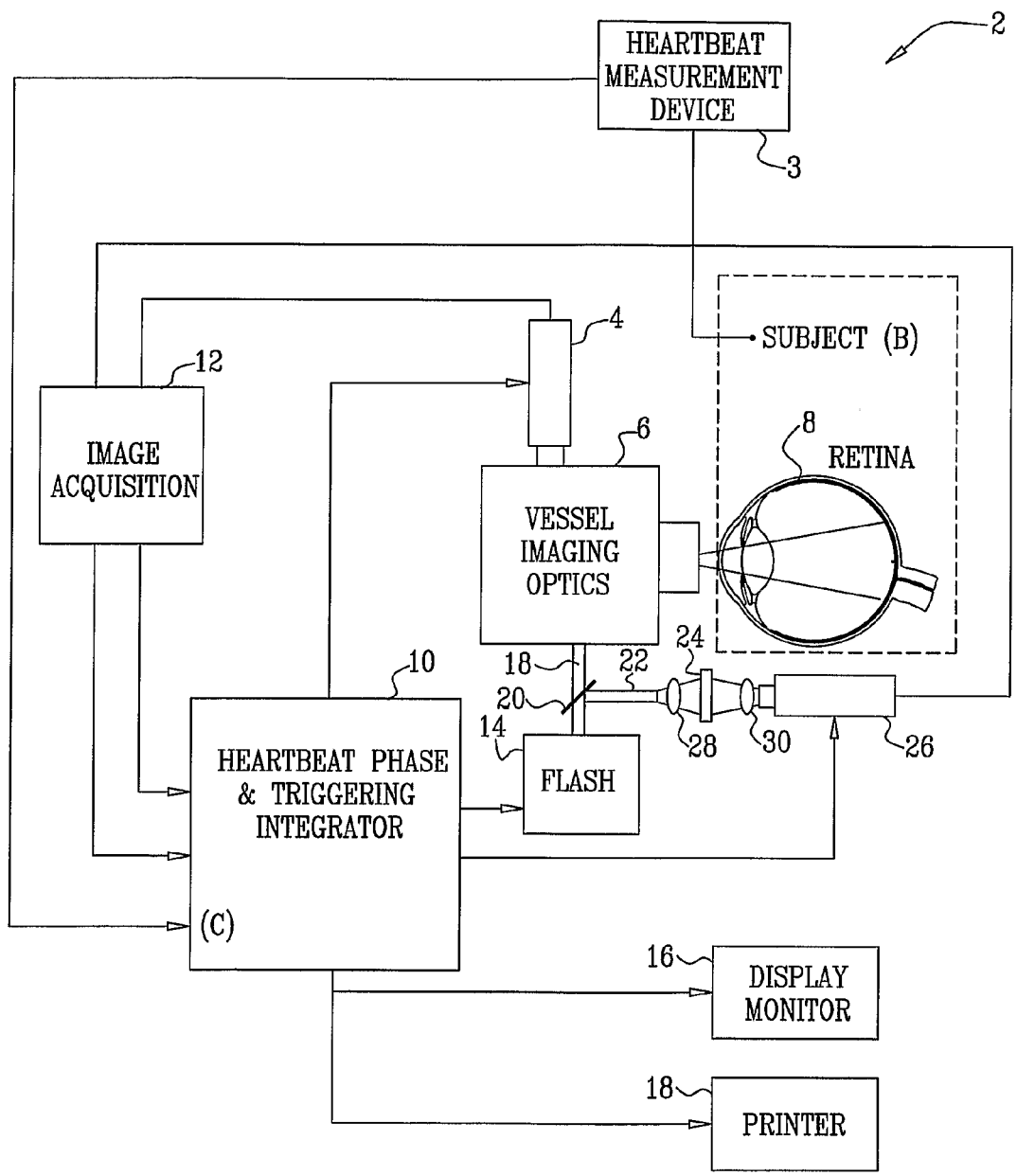
FIG. 1 is a block diagram of measurement apparatus for non-invasively measuring the blood flow rate in a blood vessel of a patient, in accordance with an embodiment of the present invention.

FIG. 1 is a block diagram of measurement apparatus 2 for non-invasively measuring the blood flow rate in a blood vessel of a patient, in accordance with an embodiment of the present invention. For illustrative purposes, the specification relates mainly, as a practical example, to such measurements performed in the retina of an eye 8. Measurement apparatus 2 typically comprises an optical measurement device that comprises vessel imaging optics 6, such as a fundus camera or an opthalmoscope for viewing retinal vessels, a flash 14, and an imager 4 (e.g., a CCD camera). Image data are sent to a "heartbeat phase and triggering integrator" unit 10 through an image acquisition interface 12, for example, a digital frame grabber. Integrator unit 10 controls image acquisition and illumination timing by means of flash 14. For some applications, a display monitor 16 is provided for viewing the results of automatic image analysis and permitting interactive image analysis, and a printer 18 generates hard copy output of analysis results.

Integrator unit 10 typically comprises (a) dedicated circuitry to input timing and data signals, process these signals, and output timing and data signals, and/or (b) one or more programmable units (e.g., embodied in a programmable digital data processor), configured to input timing and data signals, process these signals, and output timing and data signals. Other components of measurement apparatus 2, in accordance with an embodiment of the present invention, are described in the above-referenced U.S. Pat. No. 6,588,901 to Grinvald et al., which is incorporated herein by reference. These components are described with reference to FIG. 1 of the '901 patent, and appear in FIG. 1 of the present patent application using the same reference numbers. Additionally, all embodiments described herein are suitable for practice in combination with techniques and apparatus described in the '901 patent, as well as with other optical blood velocity measurement apparatus known in the art.

Measurement apparatus 2 additionally comprises a heartbeat measurement device 3, comprising, for example, a pulse oximeter, an electrocardiograph or an optical densitometer suitable for temporary coupling to a finger or earlobe of the patient. This list of devices is intended to be indicative only, and not exhaustive or exclusive.

Heartbeat measurement device 3 typically has a digital output (C), such as a TTL pulse, having a temporal characteristic which has a determinable relationship to the heartbeat cycle itself. For example, the temporal characteristic may be the moment of a low to high voltage transition of the TTL pulse, and this may indicate the end of the QRS complex. Alternatively, the output of heartbeat measurement device 3 varies continuously, providing more complete information about the heartbeat cycle. In this case, integrator unit 10 typically analyzes the output of device 3 to determine a repeating, fixed point in the cardiac cycle.

With knowledge of the patient's cardiac cycle, operation of flash 14 is timed such that light is delivered and images acquired during a known phase of the patient's heartbeat cycle. These embodiments address the technical challenge that the rate of blood flow through all blood vessels varies substantially over the course of a heartbeat cycle. Since some sampling periods for use with the apparatus described in the '901 patent are much shorter than a heartbeat cycle, the embodiments described herein give the ability to control when in the heartbeat cycle flash 14 is activated and a measurement is taken. For some applications, flash 14 is activated independently of the cardiac cycle, and subsequent analysis of the images acquired also accesses the data from heartbeat measurement device 3, in order to reject images not acquired during a designated window of the cardiac cycle.

In an embodiment, flash 14 is activated at a fixed time after a known feature of the cardiac cycle, for example, immediately upon sensing the QRS complex, or within 1-100 ms, 100-300 ms, or 300-900 ms after the peak of the QRS complex.

Using this simple algorithm, however, some level of inaccuracy may be obtained, because when the patient's heart rate is rapid, flash 14 may be activated at a later relative phase in the cardiac cycle than when the patient's heart rate is slow. Thus, for example, although activating flash 14 at a fixed time after the previous QRS complex produces acceptable results in embodiments of the present invention in which it is desired to activate flash 14 shortly before systole (e.g., about 100-200 ms before the QRS complex), improvements in accuracy can be obtained using techniques described hereinbelow.

Measuring blood flow velocity just before systole, as provided by these embodiments of the present invention, provides a stable baseline level of blood flow velocity, at the slowest time in the cardiac cycle. For some applications, it is desirable to measure the variability of blood flow velocity during the cardiac cycle, in which case measurement apparatus 2 is programmed to activate flash 14 just before systole during some heartbeats, and just after systole (e.g., about 0-100 ms after the QRS complex) during other heartbeats. In an embodiment, heartbeat measurement device 3 operates during data acquisition periods, but is not used as a trigger for data acquisition. Instead, data are acquired independently of the cardiac cycle. During post-processing of the data, velocity measurements are binned according to where in the cardiac cycle they were measured.

Figure 2:
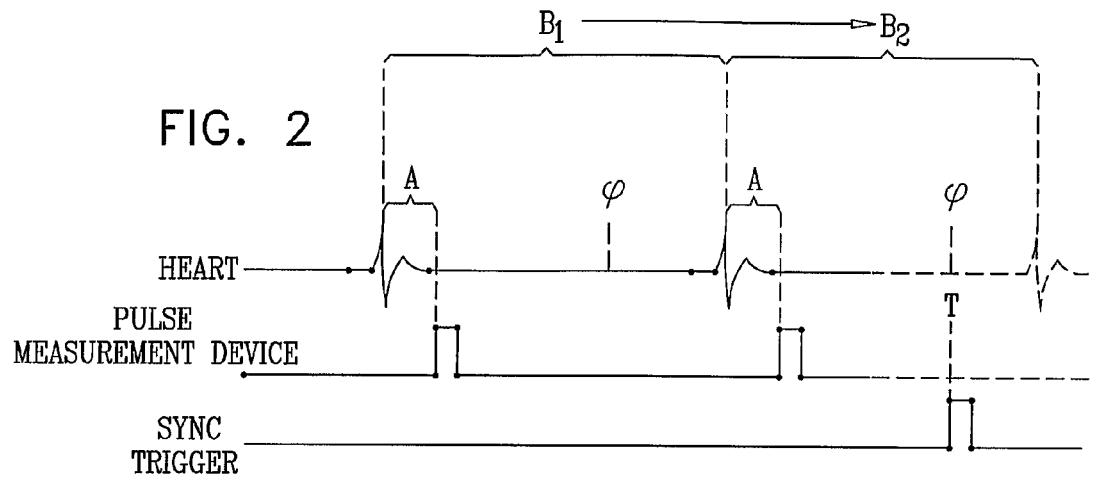
FIG. 2 is a sample graph representing a technique for initiating data acquisition at a time fixed to a particular phase of the cardiac cycle, in accordance with an embodiment of the present invention.

FIG. 2 is a sample graph representing a technique for initiating data acquisition at a time fixed to a particular phase of the cardiac cycle, in accordance with an embodiment of the present invention. Measurement apparatus 2 (in this case, integrator unit 10 or heartbeat measurement device 3) assesses the instantaneous heart rate of the patient by measuring the interval between the two most recent heartbeat measurement device outputs. (Alternatively, an average or other combination of recent heartbeat cycle durations is used.) At the end of the first heartbeat shown in FIG. 2, measurement apparatus 2 assesses the instantaneous heart rate. This heart rate is represented in the figure by its inverse, duration B1. Measurement apparatus 2 is typically preprogrammed to attempt to activate flash 14 at a designated phase of the cardiac cycle, i.e., at a point $\phi$ in the cycle, where $\phi$ could be defined by being, for example, about 10% or about 75% of the cardiac cycle following the QRS complex. The time A between sensing by heartbeat measurement device 3 of the QRS complex and the output by device 3 of a pulse is typically fixed. Thus, upon measuring the instantaneous heart rate B1, and typically in an early stage of the second heartbeat, integrator unit 10 calculates a data acquisition triggering time (T) at which flash 14 will be activated and image acquisition will begin. If the second heartbeat is subsequently measured to have a duration B2 that is close to B1 (e.g., 1−MIN(B1,B2)/MAX(B1,B2)<about 10% or 20%) then the image data acquired at time T are stored. If the second heartbeat is measured to have a duration B2 that is not similar to B1 (e.g., 1−MIN(B1,B2)/MAX(B1,B2)>about 40% or 50%), then the image data acquired at time T are typically rejected, or set aside. Alternatively or additionally, small but non-trivial deviations between B1 and B2 are identified and a correction algorithm is applied to the recorded data, as described hereinbelow.

Figure 3:
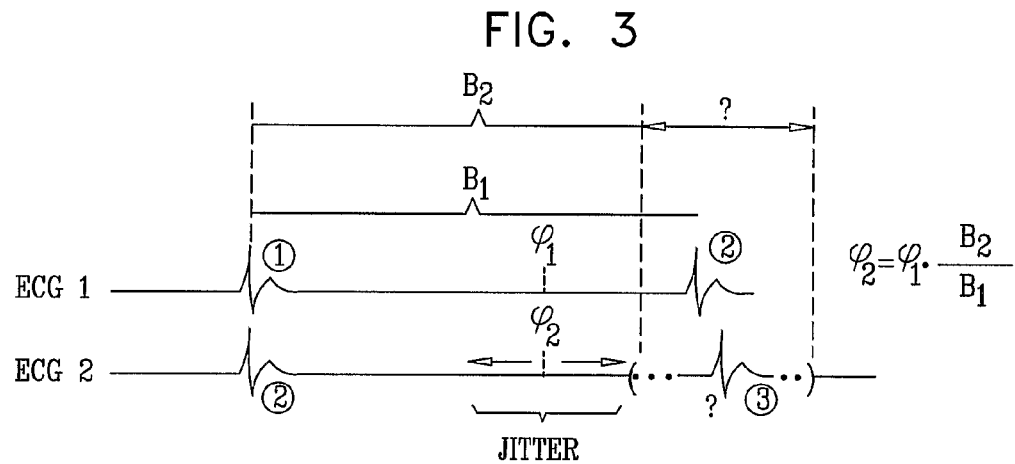
FIGS. 3 and 4 are sample graphs representing a technique for correcting velocity data, in accordance with an embodiment of the present invention.
Figure 4:
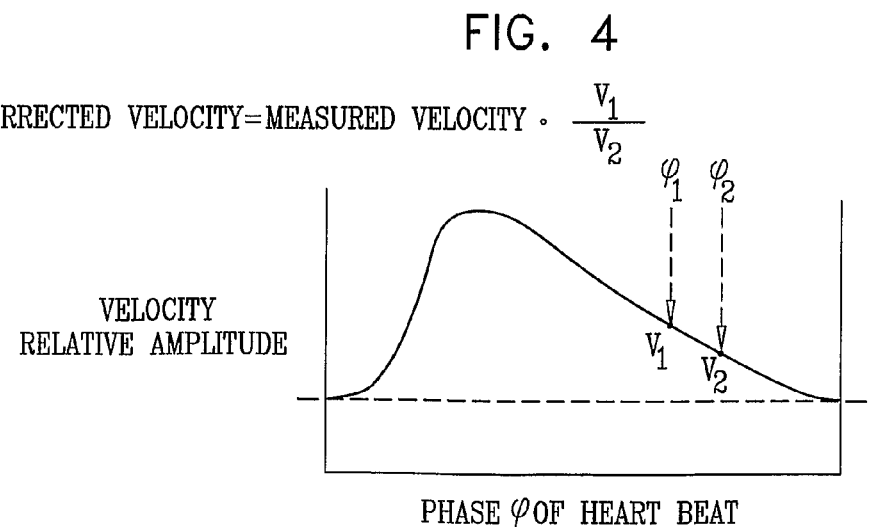

Reference is now made to FIGS. 3 and 4, which are sample graphs representing a technique for correcting velocity data, in accordance with an embodiment of the present invention. Sometimes, integrator unit 10 determines that the heartbeat cycle during which data acquisition occurred was somewhat longer or shorter than the previously measured heartbeat cycle. In other words, B2 (on ECG 2, the time between pulse 2 and pulse 3) is somewhat longer or shorter than B1 (on ECG 1, the time between pulse 1 and pulse 2). Thus, a corresponding phase error will have occurred because $\phi 2$ for the second heartbeat was not the same as $\phi 1$ for the first heartbeat. Since blood flow velocity varies as a function of the cardiac cycle, this phase error could introduce some measurement error in the blood flow velocity measurement. That is, some amount of "jitter" exists in the measured data due to variations in heart rate.

In a first method to reduce the phase error, integrator unit 10 calculates (typically but not necessarily during a post-processing session after all data have been acquired) the duration B2 of the heartbeat cycle during which the data were actually taken. From this, and the information already available, integrator unit 10 calculates at what phase in the heartbeat cycle data acquisition actually occurred. Combining with this measurement previously gathered knowledge of how blood velocity generally varies in subjects as a function of heartbeat cycle (e.g., as shown in FIG. 4), integrator unit 10 corrects the measured velocity so that it approximately reflects the velocity that would have been measured, if the duration of the second heartbeat had been known in advance and the measurement had been made at the desired phase in the second heartbeat.

Thus, for example, if the second heartbeat were shorter than predicted, the velocity measurement will be seen with hindsight to have been made at a later phase in the second heartbeat than desired. In the sample data shown in FIG. 4, the measured velocity was lower than the velocity at the desired phase. In order to estimate the velocity at the desired phase, a correction factor is applied to the measured velocity. In the example of FIG. 4, a predetermined population-based velocity calibration curve is known, and is used to generate the correction factor.

In a second method to reduce the phase error, which may be practiced in combination with the first method, short-term trends of heart rate are assessed, and serve as inputs to the algorithm of integrator unit 10 that predicts the length of a subsequent heartbeat. An example of this method is described hereinbelow with reference to FIG. 5.

Figure 5:
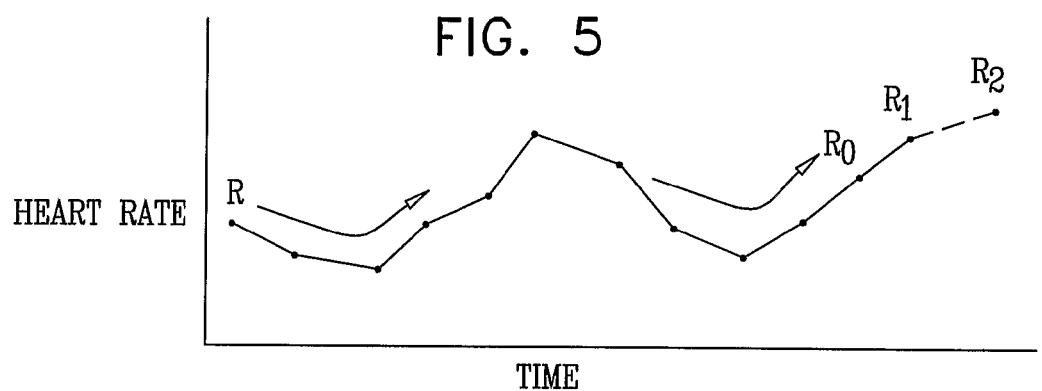
FIG. 5 is a sample graph representing a technique for reducing phase error, in accordance with an embodiment of the present invention.

FIG. 5 is a sample graph representing a technique for reducing phase error, in accordance with an embodiment of the present invention. For many individuals (in particular sedentary patients), heartbeat cycle time does not increase and decrease randomly, but rather sinusoidally, roughly as a function of the current phase of the patient's respiratory cycle. FIG. 5 shows sample data reflecting this phenomenon. Thus, by analyzing the recent history of the patient's heart rate (e.g., from rate R to R1 in the figure), integrator unit 10 identifies periodic rises and falls in the heart rate and predicts whether the next heartbeat in sequence (R2, in the figure) will be faster or slower than the previous one, and approximately by how much.

Therefore, for some applications, prediction based upon the instantaneous heart rate as described hereinabove with reference to FIG. 2 is replaced by or supplemented by (e.g., with weighting of 50% per strategy) a model that looks at recent short-term variations in heart rate.

Figure 6:
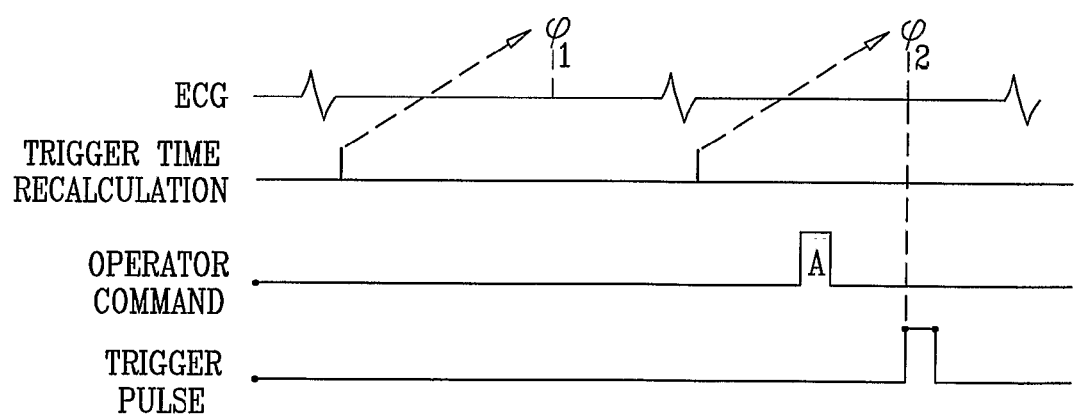
FIG. 6 is a sample graph representing a technique for timing data acquisition in response to an operator command, in accordance with an embodiment of the present invention.

FIG. 6 is a sample graph representing a technique for timing data acquisition in response to an operator command, in accordance with an embodiment of the present invention. Typically, an operator enters a command in order to initiate data acquisition, after checking that the patient is ready and that measurement apparatus 2 is ready and well positioned with respect to the patient. It is desirable to avoid a long delay between the operator entering the command to acquire an image (e.g., by pressing a start button), and the actual acquisition of the image. Long delays sometimes tend to degrade the quality of the data acquired (for example, the patient's eye may move). Some embodiments of the present invention both improve heartbeat synchronization, as described herein, and minimize the delay between the operator command and the acquisition of data.

In accordance with an embodiment of the present invention, integrator unit 10 calculates potential times to trigger flash 14 on a continuous, rolling basis. Integrator unit 10 knows in advance the time at which the next data acquisition should occur if an operator command is received, and continuously prepares itself to acquire data during the current heartbeat cycle, if possible, or else in the next heartbeat cycle. If the operator command is not received, then integrator unit 10 does not trigger the optical measurement device to acquire data when the trigger point is reached (at time $\phi 1$ in FIG. 6). If in the next heartbeat the operator command is received (at time A in FIG. 6), then there is no need to wait until the next pulse from the heartbeat measurement device, as the trigger is already set (to time $\phi 2$ in FIG. 6). In this manner, the optical measurement device is continuously pre-primed, and so the latency from operator command to image acquisition is generally one heartbeat cycle or less.

Figure 7:
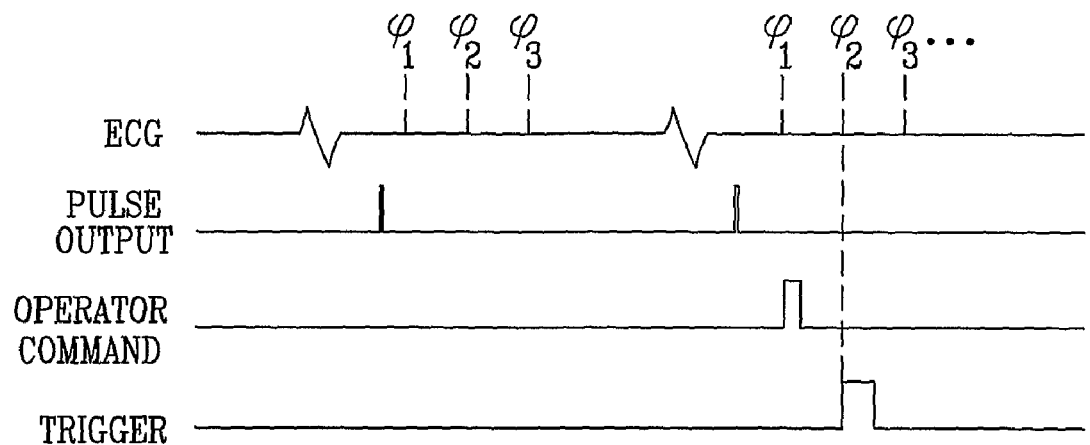
FIG. 7 is a sample graph representing a technique for reducing the latency between an operator command and activation of the optical measurement device, in accordance with an embodiment of the present invention.

FIG. 7 is a sample graph representing a technique for reducing the latency between an operator command and activation of the optical measurement device, in accordance with an embodiment of the present invention. Under certain circumstances, it is advantageous to have more than one "target point" set during a heartbeat cycle when it is suitable to actuate the optical measurement device to acquire data. There is, for example, a long period preceding the ECG spike during which the rate of blood flow changes relatively little. In FIG. 7, three target points are identified as ($\phi 1$, $\phi 2$, and ($\phi 3$. As shown in the sample graph of FIG. 7, no operator command was received during the first heartbeat, but shortly after ($\phi 1$, an operator command was received. Therefore, a trigger was generated in order to initiate data acquisition at $\phi 2$. With slight normalizing adjustments analogous to those described hereinabove with reference to FIG. 4, or by simply accepting the slight extra variability introduced, integrator unit 10 in many cases reduces the latency between operator command and image acquisition to substantially less than a heartbeat cycle.

It is noted that for many embodiments, the target points occupy a continuous range of time, e.g., extending from $\phi 1$ to $\phi 3$, rather than a small number of discrete points. For other embodiments, a number of target points are distributed at different portions of the cardiac cycle, in order to facilitate measurements of, for example, maximum and minimum blood flow velocity.

For embodiments in which techniques described herein are practiced (e.g., the embodiment described with reference to FIG. 7), integrator unit 10 typically stores the actual instantaneous heart rate of the patient during data acquisition and the point in the heartbeat when data were acquired (e.g., the number of milliseconds after the QRS complex).

Figure 8:
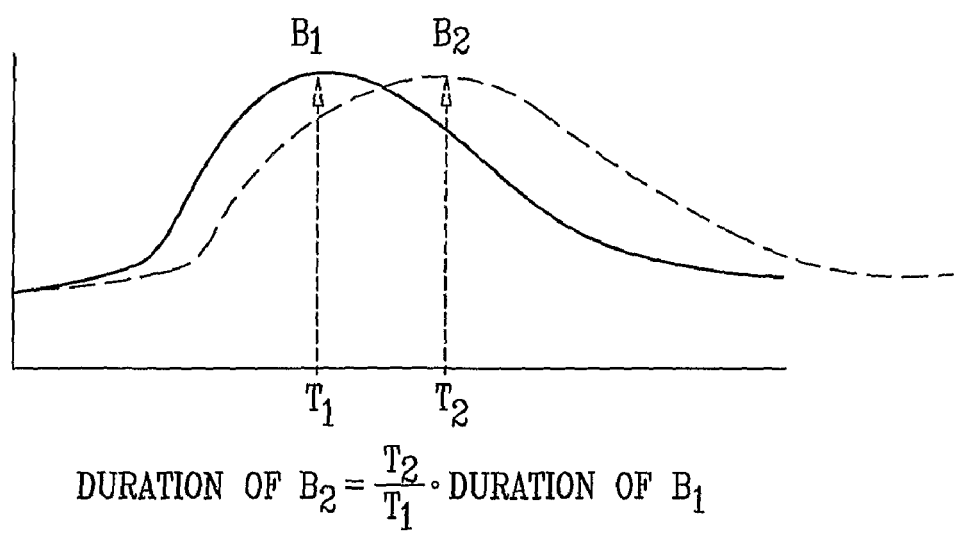
FIG. 8 is a sample graph representing a method for enhancing phase accuracy, in accordance with an embodiment of the present invention.

FIG. 8 is a sample graph representing a method for enhancing phase accuracy, in accordance with an embodiment of the present invention. For some applications, heartbeat measurement device 3 comprises an electrocardiograph (ECG) or other generator of a continuously-varying trace of cardiac activity. In an embodiment, integrator unit 10 compares the state of the trace which begins at the onset of the current heartbeat cycle (however defined) to a reference trace that was output during the most recent complete cycle, or some combination of recent cycles. The comparison may comprise, for example, expanding the reference trace in time until it best matches the current partial trace, and noting how much expansion is required to obtain that match. Alternatively, the current partial trace is expanded until it best matches the reference trace. An example of such expansion is shown in FIG. 8. Integrator unit 10 lines up the reference and current partial traces post-expansion, and assesses (a) how long the current heartbeat is going to last, and (b) when during the current heartbeat the optical measurement device should be activated to begin data acquisition.

It is noted that although embodiments described herein relate specifically to cardiac cycle synchronization of the acquisition of images of blood vessels for the purpose of blood flow velocity measurement, the scope of the present invention include synchronization of data acquisition to other measurable, cyclic physiological parameters, such as the respiratory cycle. (For example, measurements of blood oxygen levels or control of a ventilator may be synchronized to a patient's natural respiratory cycle, using techniques described hereinabove, mutatis mutandis.) Similarly, the scope of the present invention includes applying the techniques described herein to facilitate synchronized measurements of blood flow in a range of optically-accessible vascular beds, including those in:

retina, conjunctiva, episclera, and tongue (and, generally, any surface-accessible vascular bed);

esophagus, stomach, small intestine, and colon (and, generally, the internal surface of the gastrointestinal tract or any vascularized passageway);

heart, brain, liver (and, generally, the surface of any surgically-accessible organ); and any vascular bed to which it is possible to gain optical access by any technique or apparatus which provide for both illumination and image capture (e.g., catheter, endoscopy, microendoscopy, or laparoscopy).

The scope of the present invention includes other techniques for reducing jitter and latency in synchronization that would be obvious to a person of ordinary skill in the art who has read the present patent application.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus, comprising:
a heartbeat measurement device, which is operative to sense a cardiac parameter of a patient and to generate a cardiac parameter signal responsively thereto;
an optical measurement device, which is operative to:
acquire images of erythrocytes within a blood vessel of the patient by emitting towards the blood vessel of the patient 400-1000 nm light, and receiving light reflected from the blood vessel, and
analyze movement of the erythrocytes within the blood vessel by processing the images; and
an integrator unit, which is operative to receive the cardiac parameter signal and, in response thereto, to actuate the optical measurement device to acquire the images,
wherein the heartbeat measurement device comprises an optical densitometer.

2. Apparatus, comprising:
a heartbeat measurement device, which is operative to sense a cardiac parameter of a patient and to generate a cardiac parameter signal responsively thereto;
an optical measurement device, which is operative to:
acquire images of erythrocytes within a blood vessel of the patient by emitting towards the blood vessel of the patient 400-1000 nm light, and receiving light reflected from the blood vessel, and
analyze movement of the erythrocytes within the blood vessel by processing the images; and
an integrator unit, which is operative to receive the cardiac parameter signal and, in response thereto, to actuate the optical measurement device to acquire the images,
wherein the cardiac parameter signal includes a varying trace indicative of a plurality of parameters of a single heartbeat, wherein the heartbeat measurement device is operative to generate the varying trace, and
wherein the integrator unit is operative to estimate a duration of a current, not yet completed, heartbeat responsively to (a) a portion of the varying trace indicative of parameters of a completed previous heartbeat, and (b) a portion of the varying trace indicative of parameters of the current heartbeat.

3. The apparatus according to claim 2, wherein the optical measurement device comprises a fundus camera.

4. The apparatus according to claim 2, wherein the optical measurement device comprises an ophthalmoscope.

5. The apparatus according to claim 2, wherein the heartbeat measurement device comprises an electrocardiograph.

6. The apparatus according to claim 2, wherein the heartbeat measurement device comprises a pulse oximeter.

7. The apparatus according to claim 2, wherein the blood vessel includes a blood vessel of a retina of the patient, and the optical measurement device is operative to receive light reflected from the blood vessel of the retina.

8. The apparatus according to claim 2, wherein the blood vessel includes a blood vessel of a tissue selected from the group consisting of: conjunctiva, episclera, tongue, a surface-accessible vascular bed, esophagus, stomach, small intestine, colon, an internal surface of a gastrointestinal tract, a vascularized passageway, heart, brain, liver, a surface of a surgically-accessible organ, and a vascular bed to which access is obtained by catheter, endoscopy, microendoscopy, or laparoscopy, and wherein the optical measurement device is operative to receive light reflected from the blood vessel of the selected tissue.

9. The apparatus according to claim 2, wherein the integrator unit is operative to designate a time for actuating the optical measurement device responsively to timing data from the heartbeat measurement device indicative of a duration of a prior heartbeat.

10. The apparatus according to claim 9, wherein the integrator unit is operative to receive during the current heartbeat an operator command from a human operator, indicating a readiness to acquire data, and to actuate the optical measurement device to acquire the data during the current heartbeat, responsively to the timing data indicative of the duration of the prior heartbeat.

11. The apparatus according to claim 9, wherein the integrator unit is operative to receive during the current heartbeat an operator command from a human operator, indicating a readiness to acquire data, and to actuate the optical measurement device to acquire the data during a heartbeat immediately following the current heartbeat, responsively to the timing data indicative of the duration of the prior heartbeat.

12. The apparatus according to claim 9,
wherein the designated time includes a plurality of designated times,
wherein the integrator unit is operative to designate the plurality of times as suitable for actuating the optical measurement device responsively to the timing data, and
wherein the integrator unit is operative to receive an operator command from a human operator, indicating a readiness to acquire data, and to actuate the optical measurement device to acquire the data at one of the designated times, responsively to the operator command.

13. The apparatus according to claim 9, wherein the integrator unit is operative to designate the time responsively to timing data indicative of a trend relating durations of a plurality of previous heartbeats.

14. The apparatus according to claim 9, wherein the integrator unit is operative to designate the time for actuating the optical measurement device responsively to timing data from the heartbeat measurement device indicative of a duration of an immediately previous heartbeat.

15. Apparatus, comprising:
a heartbeat measurement device, which is operative to sense a cardiac parameter of a patient and to generate a cardiac parameter signal responsively thereto;
an optical measurement device, which is operative to:
  acquire images of erythrocytes within a blood vessel of the patient by emitting towards the blood vessel of the patient 400-1000 nm light, and receiving light reflected from the blood vessel, and
  analyze movement of the erythrocytes within the blood vessel by processing the images; and
an integrator unit, which is operative to receive the cardiac parameter signal and, in response thereto, to actuate the optical measurement device to acquire the images,
wherein the integrator unit is operative to designate the time for actuating the optical measurement device responsively to timing data from the heartbeat measurement device indicative of a duration of an immediately previous heartbeat, and
wherein the integrator unit is operative to:
  (a) actuate the optical measurement device at the designated time during a current heartbeat,
  (b) subsequently determine the duration of the current heartbeat,
  (c) process data acquired by the optical measurement device according to a first protocol if the duration of the previous heartbeat differs from the duration of the current heartbeat by less than a threshold value, and
  (d) process data acquired by the optical measurement device according to a second protocol if the duration of the previous heartbeat differs from the duration of the current heartbeat by more than the threshold value.

16. The apparatus according to claim 15, wherein the cardiac parameter signal includes a digital pulse indicative of a heartbeat, and wherein the heartbeat measurement device is operative to generate the digital pulse and not to generate, every heartbeat, additional information indicative of a measured parameter of the heartbeat.

17. The apparatus according to claim 15, wherein to carry out the first protocol the integrator unit is operative to designate the acquired data as good data.

18. The apparatus according to claim 15, wherein to carry out the first protocol the integrator unit is operative to process and output the acquired data for display to a human operator.

19. The apparatus according to claim 15, wherein the integrator unit is operative to determine that the duration of the previous heartbeat (Dp) and the duration of the current heartbeat (Dc) differ by less than the threshold value if 1−MIN(Dp,Dc)/MAX(Dp,Dc) is less than 0.20.

20. The apparatus according to claim 15, wherein the integrator unit is operative to determine that the duration of the previous heartbeat (Dp) and the duration of the current heartbeat (Dc) differ by less than the threshold value if ABS(Dp−Dc) is less than 50 ms.

21. The apparatus according to claim 15, wherein to carry out the second protocol the integrator unit is operative to discard the acquired data.

22. The apparatus according to claim 15, wherein to carry out the second protocol the integrator unit is operative to correct the acquired data, and output the corrected data for display to a human operator.

23. The apparatus according to claim 22, wherein the integrator unit is operative to analyze the acquired data to generate an indicator of blood flow velocity, and to correct the indicator of blood flow velocity by a factor that is based on a known relationship between typical blood flow velocities at a plurality of phases of a cardiac cycle.

24. Apparatus, comprising:
a heartbeat measurement device, which is operative to sense a cardiac parameter of a patient and to generate a cardiac parameter signal responsively thereto:
an optical measurement device, which is operative to acquire data by emitting light towards tissue of the patient and receiving light reflected from the tissue; and
an integrator unit, which is operative to:
  receive the cardiac parameter signal,
  designate one or more designated times as suitable for actuating the optical measurement device responsively to the timing data from the heartbeat measurement device indicative of a duration of a prior heartbeat,
  receive an operator command from a human operator, indicating a readiness to acquire data, and
  actuate the optical measurement device to acquire the data at one of the designated times, responsively to the operator command,
wherein the integrator unit is operative to:
  (a) actuate the optical measurement device at the one of the designated times during a current heartbeat, responsively to the operator command,
  (b) subsequently determine the duration of the current heartbeat,
  (c) process data acquired by the optical measurement device according to a first protocol if the duration of the previous heartbeat differs from the duration of the current heartbeat by less than a threshold value, and
  (d) process data acquired by the optical measurement device according to a second protocol if the duration of the previous heartbeat differs from the duration of the current heartbeat by more than the threshold value.

25. The apparatus according to claim 24, further comprising a button for pressing by the human operator, wherein the integrator unit is operative to receive the operator command from the human operator responsively to the operator pressing the button.

26. The apparatus according to claim 24, wherein the integrator unit is operative to designate the one or more times responsively to timing data indicative of a trend relating durations of a plurality of previous heartbeats.

27. The apparatus according to claim 24, wherein the integrator unit is operative to designate the one or more times for actuating the optical measurement device responsively to timing data from the heartbeat measurement device indicative of a duration of an immediately previous heartbeat.

28. The apparatus according to claim 24, wherein to carry out the first protocol the integrator unit is operative to designate the acquired data as good data.

29. The apparatus according to claim 24, wherein to carry out the second protocol the integrator unit is operative to discard the acquired data.

* * * * *